(12) United States Patent
Dubrowskij

(10) Patent No.: US 6,796,203 B2
(45) Date of Patent: Sep. 28, 2004

(54) ROTATION JOINT, ESPECIALLY FOR MEDICAL INSTRUMENTS

(75) Inventor: Arkadij Veniaminowitsch Dubrowskij, Moscow (RU)

(73) Assignee: Karl Stroz GmbH & Co. KG (DE)

( * ) Notice: Subject to any disclaimer, the term of this patent is extended or adjusted under 35 U.S.C. 154(b) by 0 days.

(21) Appl. No.: 10/121,829

(22) Filed: Apr. 12, 2002

(65) Prior Publication Data
US 2003/0032948 A1 Feb. 13, 2003

Related U.S. Application Data

(63) Continuation of application No. PCT/DE99/03337, filed on Oct. 14, 1999.

(51) Int. Cl.[7] .................................................. B25J 17/02
(52) U.S. Cl. ................... 74/490.05; 74/423; 74/490.06; 901/28
(58) Field of Search .............................. 74/423, 490.08, 74/490.06; 901/28, 29

(56) References Cited

U.S. PATENT DOCUMENTS

| 4,641,657 | A | | 2/1987 | Ellis |
| 4,662,815 | A | * | 5/1987 | Zimmer ...................... 414/735 |
| 4,690,012 | A | * | 9/1987 | Dahlquist et al. ........ 74/490.06 |
| 4,771,652 | A | * | 9/1988 | Zimmer ....................... 74/640 |
| 4,990,050 | A | * | 2/1991 | Tsuge et al. ................ 414/735 |
| 5,209,747 | A | | 5/1993 | Knoepfler |
| 5,549,637 | A | | 8/1996 | Crainich |
| 5,575,799 | A | | 11/1996 | Bolanos et al. |
| 5,761,965 | A | * | 6/1998 | Dahlquist ................ 74/490.03 |
| 5,772,655 | A | | 6/1998 | Bauer et al. |

FOREIGN PATENT DOCUMENTS

| CH | WO 992/21686 | 5/1999 | |
| DE | 3601456 A1 | * 7/1986 | ............ B25J/17/00 |

* cited by examiner

Primary Examiner—David A. Bucci
Assistant Examiner—Timothy McAnulty
(74) Attorney, Agent, or Firm—St. Onge Steward Johnston & Reens LLC

(57) ABSTRACT

The invention relates to a rotation joint, especially for medical instruments, with a proximal and a distal part that are coupled to one another by means of a gear work and can be adjusted in relation to one another between a non-deflected starting position and an angled end position, where the gear work is housed in an intermediate part situated between the proximal and the distal parts and all three parts have at least one hollow center channel. In order to create a rotation joint that can be actuated by a non-angled position and can be secured in the deflected position, the invention proposes that the proximal part consists of two tubes that are arranged coaxially inside one another and can rotate in opposite directions around their longitudinal axis, where at least the outer tube is connected with a handle on its proximal side.

5 Claims, 2 Drawing Sheets

ROTATION JOINT, ESPECIALLY FOR MEDICAL INSTRUMENTS

This application is a continuation of pending International Application PCT/DE99/03337 filed on Oct. 14, 1999 designating the United States.

FIELD OF THE INVENTION

The invention relates to a rotation joint, especially for medical instruments, with a proximal and a distal part that are coupled to one another by means of a gear work and can be adjusted in relation to one another between a non-deflected starting position and an angled end position, where the gear work is housed in an intermediate part situated between the proximal and the distal parts and all three parts have at least one hollow center channel.

BACKGROUND OF THE INVENTION

Various constructions are known from medical technology which serve to alter the angle of deflection of the working parts of a medical instrument from the longitudinal axis of the housing. These known rotation joints often have the disadvantages that the change of the angle setting cannot be actuated remotely, that is, from a position distant from the actual rotation joint; or that the determined angle setting cannot be secured; and/or that the rotation joints have no hollow central channel for the purpose, for instance, of actuating the working parts on the distal end of the instrument by way of a cable pull.

A rotation joint of the aforementioned type is known, for instance, from U.S. Pat. No. 4,641,657. This familiar rotation joint has the disadvantage that the angle setting of the individual rotation joint parts to one another is changed by turning the intermediate part, so that remote operation of the rotation joint is impossible. In addition, the previously known construction has no means to secure the rotation joint in the deflected position.

SUMMARY OF THE INVENTION

On this basis, the aim of the invention is to perfect a rotation joint of the type cited at the outset in such a way that the rotation joint can be actuated from a position distant from it and that the selected angle setting of the rotation joint parts to one another can be secured.

This aim is fulfilled by the invention in that the proximal part consists of two tubes that are arranged coaxially inside one another and can rotate in opposite directions around their longitudinal axis, where at least the outer tube is connected with a handle on its proximal side.

By means of the handle connected with the outer tube of the proximal part, it is possible to displace the rotation joint by turning the outer tube without the necessity of directly displacing the intermediate part containing the gear work. In addition to the remote displacement of the rotation joint, the handle allows the rotation joint to be secured in the particular deflected position. An additional advantage of the inventive construction is that the rotation joint is very rigid because of the coaxial arrangement of the two tubes forming the intermediate part.

To ensure that the rotation joint can be rotated to the desired angle without any loss of rigidity, it is proposed in a further refinement of the invention that the terminal surfaces of the distal-side end of the proximal part and of the proximal-side end of the distal part, which surfaces are turned toward one another and, in the starting position, are adjoining the terminal surfaces of the intermediate part, are inclined toward one another at the same angle toward the longitudinal axis.

It is further proposed, through the invention, that the inner tube on the distal side is equipped with a gear wheel of the gear work and that a steering pin is mounted on the distal-side terminal end of the outer tube, where the steering pin engages into a corresponding recess of the intermediate part. Because of the invention's design of the proximal part of the rotation joint, it is possible to change the angle setting of the rotation joint by turning either the inner tube or the outer tube independently of one another.

In a preferred embodiment of the invention, it is proposed that the gear work consists of at least two beveled wheels engaged with one another, where one beveled wheel is connected with the distal-side end of the inner tube and another beveled wheel with the proximal-side end of the distal part. The use of two beveled wheels engaged with one another makes it possible to diverge the proximal and the distal ends of the rotation joint, each by the same angle to the longitudinal axis.

To achieve an especially flat curvature between the proximal part and the distal part, another means of reducing the risk of crushing the actuation material conducted through the hollow central channel, it is proposed in a second embodiment of the invention that the two beveled wheels connected with the proximal and distal parts are connected with one another by way of a beveled wheel housed in the intermediate part. The intermediate piece in this variant is extended by the radius of the additional beveled wheel, which results in a greater radius of the curvature.

Finally, it is proposed with this invention that the maximum angle of diversion of the rotation joint of this design between the starting and end positions is determined by the formula 4×(90 degrees−alpha). For a maximum angle of diversion of 90 degrees, therefore, the value for alpha is 67.5 degrees and for a maximum angle of diversion of 180 degrees the value for alpha is 45 degrees.

BRIEF DESCRIPTION OF DRAWINGS

Additional characteristics and advantages of the invention are presented in the following description of the related illustrations, which depict two models of an inventive rotation joint by way of example. The illustrations are as follows.

DETAILED DESCRIPTION OF DRAWINGS

Figure 1:
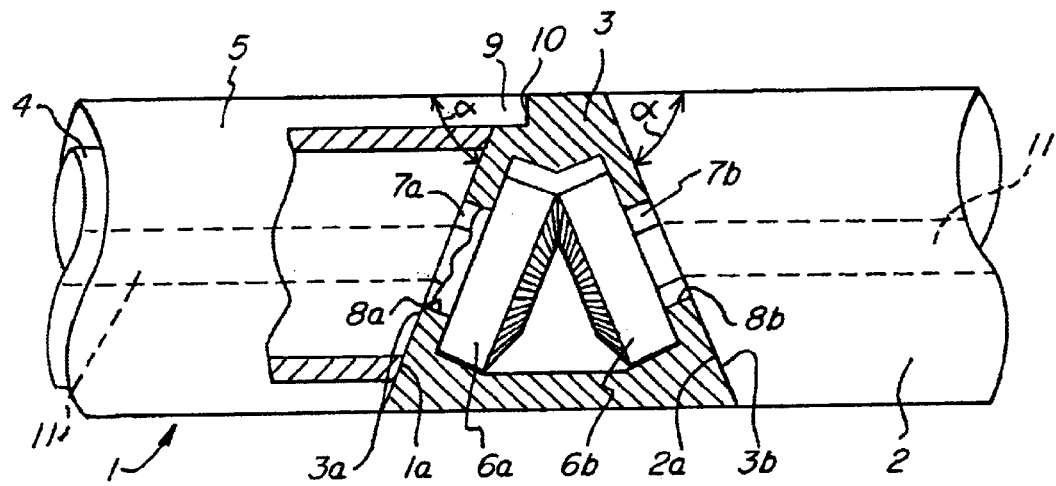
FIG. 1 Partly cut-out lateral view of an initial model of an inventive rotation joint in the non-deflected starting position.
Figure 2:
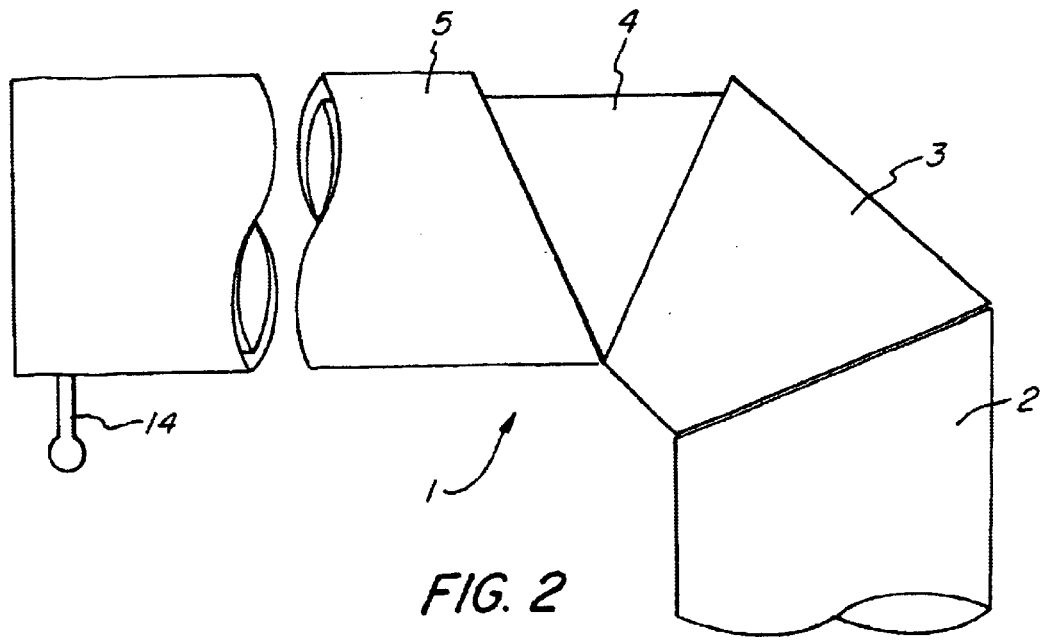
FIG. 2 Lateral view of the rotation joint according to FIG. 1 in the angled final position.

The rotation joints depicted in cut-out form in the illustrations consist basically of one proximal part 1, a distal part 2, and an intermediate part 3 situated between the proximal part 1 and the distal part 2. As can be seen in FIGS. 1 and 2, the proximal part consists of two tubes coaxially arranged inside one another, that is, an inner tube 4 and an outer tube 5.

Such rotation joints used with medical instruments serve to allow an angle of deflection of the working parts of a medical instrument from the longitudinal axis of the instrument's shaft. To make possible the displacement of the rotation joint from a non-deflected position, as is required for instance in endosurgical instruments, at least the outer tube 5 has on the proximal side a handle 14, by means of which the outer tube 5 can be rotated with respect to the inner tube 4 around the longitudinal axis of both tubes 4, 5. The handle 14 also serves to secure the rotation joint in the particular deflected position.

In the model of a rotation joint shown in FIG. 1, the proximal part 1 and the distal part 2 are coupled with one another and can be rotated with respect to one another by means of a gear work consisting of two beveled wheels 6a, 6b.

Figure 3:
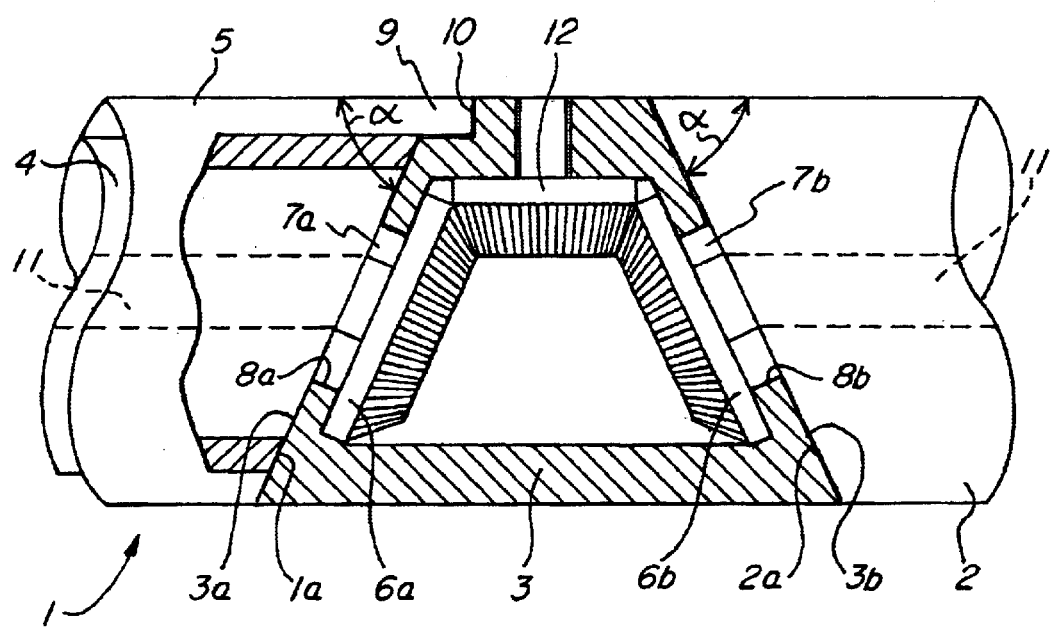
FIG. 3 Partly cut-out lateral view of a second model of an inventive rotation joint in the non-deflected starting position.

As can be seen from the starting positions shown in FIGS. 1 and 3, in which the three parts 1, 2, and 3 are not turned with respect to one another, the terminal surfaces 1a and 2a of proximal part 1 and distal part 2, turned toward one another and adjoining the terminal surfaces 3a, 3b of the intermediate part 3, are inclined together at the same angle alpha to the longitudinal axis of the rotation joint. The beveled wheels 6a, 6b, which form the gear work, are connected with the proximal part 1 and the distal part 2 by means of axis ends 7a, 7b arranged vertically on the terminal surfaces 1a of the distal-side end of the inner tube 4 and of the proximal-side end of the distal part 2. In the terminal surfaces 3a, 3b of the intermediate part 3, openings 8a, 8b corresponding to the radius of the axis end 7a, 7b are formed in such a way that the edges of the openings extend beyond the beveled wheels 6a, 6b and thus lend sufficient rigidity to the overall construction.

To move the rotation joint by means of the handle 14 connected with the proximal-side end of at least the outer tube 5, on a spot on the distal-side terminal surface 1a of the outer tube 5 a steering pin 9 is configured, which engages in a corresponding recess 10 of the intermediate part 3. As a result of turning the outer tube 5 while the inner tube 4 remains stable, the intermediate part 3 can be rotated as far as the end position shown in FIG. 2 by means of the steering pin 9. The coupled terminal surfaces 1a–3a and 3b–2a make possible the rotation of the rotation joint to the desired angle, while the rigidity of the rotation joint remains unchanged.

The same deflection of the rotation joint to the end position shown in FIG. 2 can be achieved by rotating the inner tube 4 while the outer tube 5 remains unmoved, where the exact displacement of parts 1, 2, and 3 of the rotation joint occurs by means of the beveled wheels 6a, 6b engaging with one another.

The rotation joint is distinguished in that curvature between the proximal part 1 and the distal part 2 in the maximum deflected end position shows a large radius, so that the actuation material, such as a rope, a flexible hose, or an electric current or light conductor for a medical working part, conducted through a hollow central channel 11 running through all three parts 1, 2, and 3, does not become bent or squeezed.

In the model illustrated in FIG. 3, the gear work consists of three beveled wheels, where the two beveled wheels 6a, 6b connected with the proximal part 1 and distal part 2 are connected with one another by a beveled wheel 12 housed in the intermediate part 3. In this design, since the intermediate part 3 is extended in length by the radius of the third beveled wheel 12, this version allows an even flatter curvature.

The maximum angle of deflection between the starting position and the end position is determined from the formula 4×(90 degrees–alpha). Thus, in order to desire to maintain a maximum angle of deflection of 90 degrees, the angle alpha, by which the terminal surfaces 1a and 2a are inclined together from the longitudinal axis, must be 67.5 degrees. With a value of 45 degrees for the alpha angle, the result is an angle of deflection of 180 degrees.

As can be seen from FIGS. 1 and 2, the turn angle of the external tube 5 with the steering pin 9 is an unlimited 360 degrees in any direction, where the maximum angle of deflection is achieved at a rotation of 180 degrees.

Illustration Key

1 Proximal part
1a Terminal end
2 Distal part
2a Terminal end
3 Intermediate part
3a Terminal end
4 Inner tube
5 Outer tube
6 Beveled wheel
7 Axis end
8 Opening
9 Steering pin
10 Recess
11 Hollow central channel
12 Beveled wheel
13 Angle

What is claimed is:

1. Rotation joint for medical instruments with a proximal part and a distal part that are coupled to one another by means of a gear work and can be adjusted in relation to one another between a non-deflected starting position and an angled end position, where the gear work is housed in an intermediate part situated between the proximal part and the distal part and separating these parts from one another, and all three parts have at least one hollow center channel running through them, and where the proximal part consists of two tubes that are arranged coaxially inside one another and can rotate independently of one another in opposite directions around their longitudinal axis, where at least an outer of the two tubes is connected with a handle on its proximal side distinguished in that an inner of the two tubes is equipped with a toothed wheel of the gear work and that a steering pin is mounted on the distal-side end surface of the outer of the two tubes, where the steering pin engages into a corresponding recess of the intermediate part.

2. Rotation joint according to claim 1, distinguished in that terminal surfaces of the distal-side end of the proximal part and of the proximal-side end of the distal part, which surfaces, in the starting position, adjoining the terminal surfaces of the intermediate part, are inclined toward one another at the same angle (alpha) toward the longitudinal axis.

3. Rotation joint according to claim 1, distinguished in that the gear work consists of at least two beveled wheels that are engaged with one another, where one beveled wheel is connected with the distal-side end of the inner of the two tubes and another beveled wheel is connected with the proximal-side end of the distal part.

4. Rotation joint according to claim 3, distinguished in that both beveled wheels connected with the proximal part and the distal part are connected with one another by way of a beveled wheel housed in the intermediate part.

5. Rotation joint according to claim 1, distinguished in that a maximum angle of deflection between the starting position and the end position is determined by the formula 4×(90 degrees–alpha).

* * * * *